US00PP20246P3

(12) United States Plant Patent
Hull

(10) Patent No.: US PP20,246 P3
(45) Date of Patent: Sep. 1, 2009

(54) ***TECOMA* PLANT NAMED 'MNSTAPBE'**

(50) Latin Name: ***Tecoma*×**
Varietal Denomination: Mnstapbe

(75) Inventor: George E. Hull, Phoenix, AZ (US)

(73) Assignee: Camelot Nurseries, Inc., Glendale, AZ (US)

( * ) Notice: Subject to any disclaimer, the term of this patent is extended or adjusted under 35 U.S.C. 154(b) by 64 days.

(21) Appl. No.: 11/998,344

(22) Filed: Nov. 29, 2007

(65) Prior Publication Data

US 2009/0144868 P1 Jun. 4, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Jeffrey L. Streets; Streets & Steele

(57) ABSTRACT

A new and distinct hybrid of the genus *Tecoma* is provided. This hybrid has been named 'Mnstabe' for a cultivar name. The new variety is the product of a deliberate cross of interspecific origin between two hybrid plants of the genus *Tecoma* made in 2006. Seeds from this cross were saved and planted and the new variety was selected from a block of these hybrid seedlings. The new variety displays a uniquely different flower color previously unavailable in the genus, is compact in size, and as well is generally sterile.

2 Drawing Sheets

Latin name of the genus and species of the plant claimed: *Tecoma*×.
Varietal denomination: Mnstapbe.

BACKGROUND OF THE INVENTION

The new 'Mnstabe' variety was selected by the inventor as a single plant from a block of hybrid seedlings during the course of plant breeding work in the year 2006. The hybrid seedlings were a result of a cross between an unnamed plant of *Tecoma* with another unnamed plant of *Tecoma*. The *Tecoma* parents are unpatented selections from garden populations. Seeds from this cross were saved and planted. The new variety was selected from a block of these hybrid seedlings.

BRIEF SUMMARY OF INVENTION

The new variety *Tecoma*×'Mnstabe' is distinguishable from its parents by displaying a distinctly different flower color previously unavailable in the genus *Tecoma*. This color is displayed in the interior and exterior of the corolla and is a primary distinguishing characteristic of the new variety. The distinctive yellow orange color of the corolla exterior is identified as RHS 21A along with highlights of yellow identified as RHS 21B. The yellow color of the corolla interior is identified as RHS 10A with a blush color orange yellow RHS 21B.

The seedlings were grown for about 1½ years and a selection was made based on the color of the corolla. The selected seedling was grown for 6 additional months and the distinctive color distinguished this seedling from other seedlings. Thereafter, asexual propagation of this new variety was carried out in Glendale, Ariz. by cuttings through several generations. The new variety reproduces true to type in successive generations of asexual propagation. The distinctive yellow orange color of the corolla remains constant in each successive crop of cutting-grown plants. The following detailed description is taken from plants that have been growing in container blocks for six months.

The *Tecoma*×'Mnstabe' is a bush with an upright growth habit to 1 meter. The new 'Mnstabe' variety exhibits heavy side branching similar to *Tecoma* species branching habit to achieve a plant width of 2 meters. The 'Mnstabe' plant is deciduous at temperature exposures below about 25° F. The maximum winter hardiness is USDA Zone 8.

This hybrid is not known to be susceptible to any soil borne pathogens or to any foliar disease. The plant has not been observed to suffer from any extraordinary insect infestations other than general aphid populations.

BRIEF DESCRIPTION OF THE DRAWINGS

The accompanying photographic drawings show typical specimens of plant parts of the new variety in color illustrations as nearly true as is reasonably possible to accomplish from conventional photographic procedures.

Figure 1:
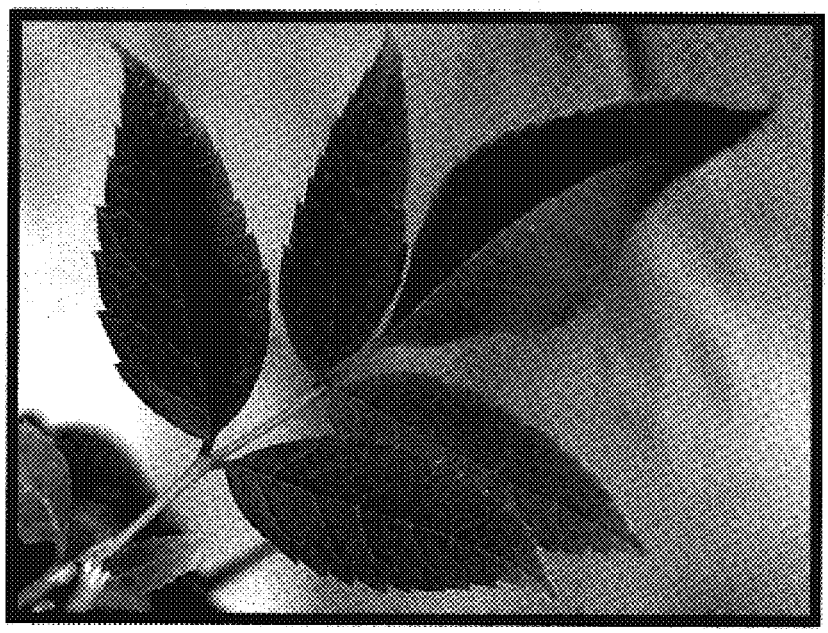
FIG. 1 shows the compound leaf and the leaflets during the summer season.
Figure 2:
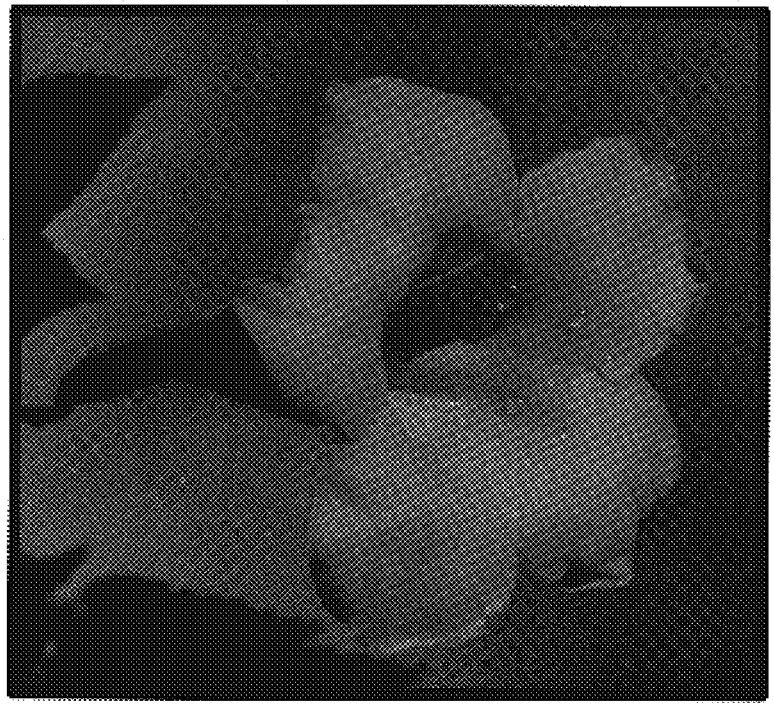
FIG. 2 shows a close up of the flower during the summer season.
Figure 3:
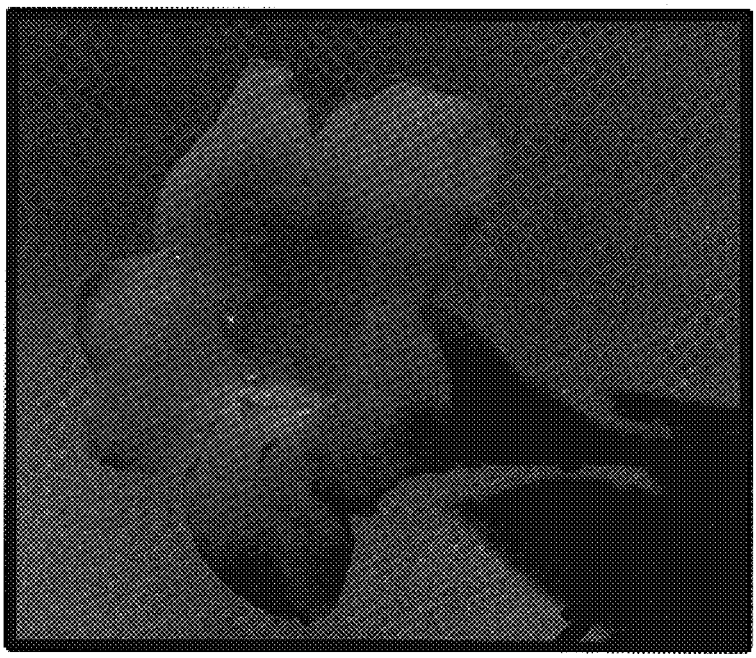
FIG. 3 shows a close up of the flower during the summer season.
Figure 4:
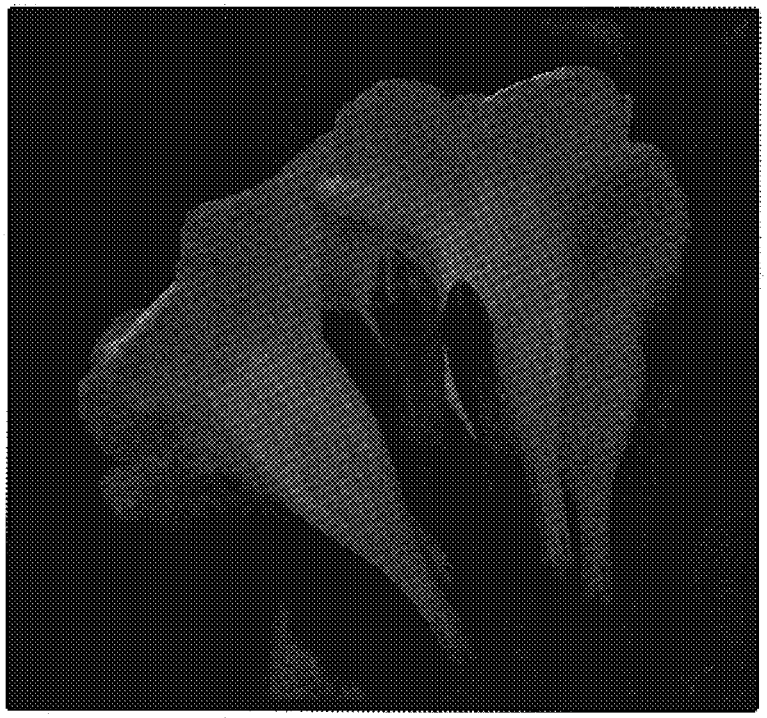
FIG. 4 shows a close up of the flower from the posterior angle during the summer season.

The color chart used in the identification of colors described herein is the RHS Colour Chart of The Royal Horticultural Society, London, England. The plants described were grown during 2006–2007 at Glendale, Ariz.

DETAILED BOTANICAL DESCRIPTION

Description of the plant:

*Classification.*—*Tecoma* Hybrid.

*Plant form.*—Bush.

*Plant height.*—To 1 meter.
*Plant width.*—To 2 meters.
*Plant growth habit.*—Perennial, upright shrub with heavy side branching similar to *Tecoma* species branching habit.
*Stem/lateral branch diameter.*—5 millimeters.
*Stem/lateral branch internode.*—4–5 centimeters.

Foliage description:
*Leaf arrangement.*—Opposite.
*Stipules.*—None.
*Petiole length.*—25–28 mm.
*Petiole diameter.*—1.5–2 mm.
*Petiole color.*—RHS 145A.
*Leaf shape.*—Odd pinnately compound.
*Leaf length.*—13–14.5 cm.
*Leaf width.*—9.6–10.5 cm.
*Leaflets.*—3–5 leaflets, ovate-lanceolate; side leaflets sessile 45–60 mm long, 20–26 mm wide; terminal leaflet 51–78 mm long, 30–35 mm wide on 10–14 mm long petiolule.
*Leaflet base.*—Unequal, obtuse.
*Leaflet apex.*—Long acuminate.
*Leaflet pubescence.*—Glabrous.
*Leaflet margin.*—Serrate.
*Leaflet color.*—Upper Surface RHS 147B, Lower Surface RHS 147C.
*Rachis color.*—RHS 145A.

Leaves are seasonally uniform in these measurements and colors except in winter when deciduous. The *Tecoma*× is generally deciduous at temperature exposures below 25° F.

Description of the flower:
*Inflorescence type.*—Raceme.
*Peduncle length.*—7–10 mm.
*Peduncle diameter.*—1 mm.
*Peduncle color.*—*RHS* 144A.
*Flower number.*—30–40.
*Calyx.*—Evenly denticulate with 6 lobes.
*Calyx shape.*—Cupular.
*Calyx length.*—5–6 mm.
*Calyx width.*—5 mm.
*Calyx pubescence.*—Glabrous.
*Calyx color.*—RHS 145A.
*Corolla shape.*—Salverform, tubular-campanulate.
*Corolla height.*—5 cm.
*Corolla tube length.*—50–55 mm long, tube salverform from 15 mm, bent at that point, then expanding to narrowly tubular-campanulate for 25 mm, lobes 15 mm by 15–17 mm wide.
*Corolla diameter.*—40 mm from lobe tip to lobe tip.
*Corolla color.*—Exterior top RHS 21A; remaining exterior RHS 21B; Interior RHS 10A with blush of RHS 21A top anterior; Guidelines interior bottom of corolla RHS 13A.
*Corolla pubescence.*—Glabrous.
*Pistil.*—3.5 mm.
*Style length.*—38 mm.
*Style color.*—RHS 11B.
*Stigma color.*—RHS 11B.
*Stigma width.*—6 mm.
*Filament number.*—5.
*Filament length.*—Anthers attached to corolla for 15 mm from base then free for 11–18 mm, thecae divicarate 3 mm.
*Filament color.*—RHS 11B.
*Pollen.*—Yes.
*Pollen color.*—RHS 11B.
*Fruit.*—None.
*Seeds.*—None.

What is claimed is:

1. A new and distinct variety of *Tecoma* plant as herein illustrated and described.

* * * * *